(12) United States Patent
Sutton

(10) Patent No.: US 6,443,950 B1
(45) Date of Patent: Sep. 3, 2002

(54) ABLATION LEAD FOR ATRIAL FLUTTER

(75) Inventor: Richard Sutton, London (GB)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/512,029

(22) Filed: Feb. 24, 2000

(30) Foreign Application Priority Data

Feb. 26, 1999 (GB) .............................................. 9904580

(51) Int. Cl.$^7$ ................................................ A61B 18/18
(52) U.S. Cl. ........................................ 606/41; 607/127
(58) Field of Search ................................ 607/101, 102, 607/122, 126, 127; 606/41, 46

(56) References Cited

U.S. PATENT DOCUMENTS

| | | | |
|---|---|---|---|
| 5,405,376 A | 4/1995 | Mulier et al. ............... | 607/127 |
| 5,582,609 A | 12/1996 | Swanson et al. ............... | 606/39 |
| 5,588,432 A | 12/1996 | Crowley ................. | 128/660.03 |
| 5,906,913 A * | 5/1999 | Mulier et al. .................. | 606/41 |
| 6,076,012 A * | 6/2000 | Swanson et al. ............... | 606/41 |

* cited by examiner

*Primary Examiner*—Linda C. M. Dvorak
*Assistant Examiner*—David M. Reddy
(74) *Attorney, Agent, or Firm*—Thomas F. Woods; Eric R. Waldkoethe; Thomas G. Benry

(57) ABSTRACT

The present invention provides an ablation lead for treating atrial flutter wherein the tip of the lead is fixed in the patient's heart by screwing and wherein the electrodes are arranged on the lead so as to overlie the area between the tricuspid annulus and the inferior vena cava. Radiofrequency energy is applied through the electrodes to cause ablation of the tissue. With the tips screwed in position, the lead can then be manipulated so that the RF energy can be applied to the area between the coronary sinus the tricuspid annulus to cause ablation of the tissue in that area also.

7 Claims, 2 Drawing Sheets

ABLATION LEAD FOR ATRIAL FLUTTER

FIELD OF THE INVENTION

The present invention relates to a method and system for treating atrial flutter.

BACKGROUND OF THE INVENTION

Atrial flutter is a common rhythm disturbance defined as an atrial tachycardia with atrial rates exceeding 240 beats per minute.

Most methods of treating atrial flutter involve pacing the heart using an appropriate pacing rate.

Use of pacing pulses delivered at multiple sites within the atria to prevent the occurrence of atrial tachyarrhythmias including atrial flutter which may in some cases progress to atrial fibrillation, has also been investigated. For example, the article "Prevention of Atrial Tachyarrhythmias related to Advanced Interatrial I Block by Permanent Atrial Resynchronisation" by Daubert et al, Pace Vol. 14, P.648, 1991, discloses the use of synchronised pacing pulses delivered to the right and left atria to prevent onset of atrial tachyarrhythmias.

Whilst appropriate pacing, using an implantable pacemaker, is suitable for treating a wide range of arrhythmias, it is not appropriate for all patients and a permanent solution for preventing atrial flutter has been sought.

WO 96/34646 to Cosio et al proposes a catheter and method for treating atrial flutter using ablation.

The action of the heart depends upon electrical signals carried along the surface of the heart tissue. Sometimes these electrical signals become faulty. It has been found that ablating or burning the cardiac conduction pathways in the region of the problem destroys the tissue to eliminate the faulty signal. Electrophysiology catheters are known for ablating certain tissue using, typically, radio frequency (RF) energy directed to one or more high energy capable ablation electrodes.

The catheter proposed by Cosio is specifically adapted for treating atrial flutter.

The ablation catheter proposed by Cosio creates a linear lesion oriented perpendicular to the isthmus of tissue between the inferior aspect of the tricuspid valve and the inferior vena cava. The invention ablates a line of tissue across the critical isthmus using ablation-capable electrodes positioned along the tip of the catheter. The catheter is designed to remain in place and provide firm electrode contact during the ablation, despite respiratory, cardiac or blood motion during ablation.

The Cosio catheter has a dual curve configuration to conform to the anatomy of the heart.

SUMMARY OF THE INVENTION

The present invention aims to allow the treatment of atrial flutter by ablation to be speeded up without giving rise to any safety problems. Speeding up the procedure results in less x-ray exposure.

According to one aspect of the present invention there is provided a method of treating atrial flutter by ablation of cardiac tissue comprising inserting an ablation lead into the heart and fixing the lead tip by screwing such that electrodes arranged on the lead overlie the area between the tricuspid annulus and the inferior vena cava; applying radiofrequency energy to that area via the electrodes to cause ablation of the tissue; manipulating the lead with the tip screwed in position such that radiofrequency energy can be applied to the area between the coronary sinus and the tricuspid annulus to cause ablation of tissue in that area.

According to a second aspect, there is provided an ablation lead for treating atrial flutter, said lead comprising a lead body; a distal tip adapted to be fixed in position in the heart; and an array of electrodes for delivering RF energy; said electrodes being arranged on the lead body such that in use the electrodes can ablate the area between the tricuspid annulus and the inferior vena cava and also the area between the coronary sinus and the tricuspid annulus without displacing the tip; and wherein the lead tip is a screw tip.

The tip is preferably adapted to be fixed in the right ventricle. The screw tip is preferably of the Bisping type without an electrode.

The preferred embodiment of the present invention will now be described, by way of example only, with reference to the accompanying drawings.

DETAILED DESCRIPTION OF THE DRAWINGS

Figure 1:
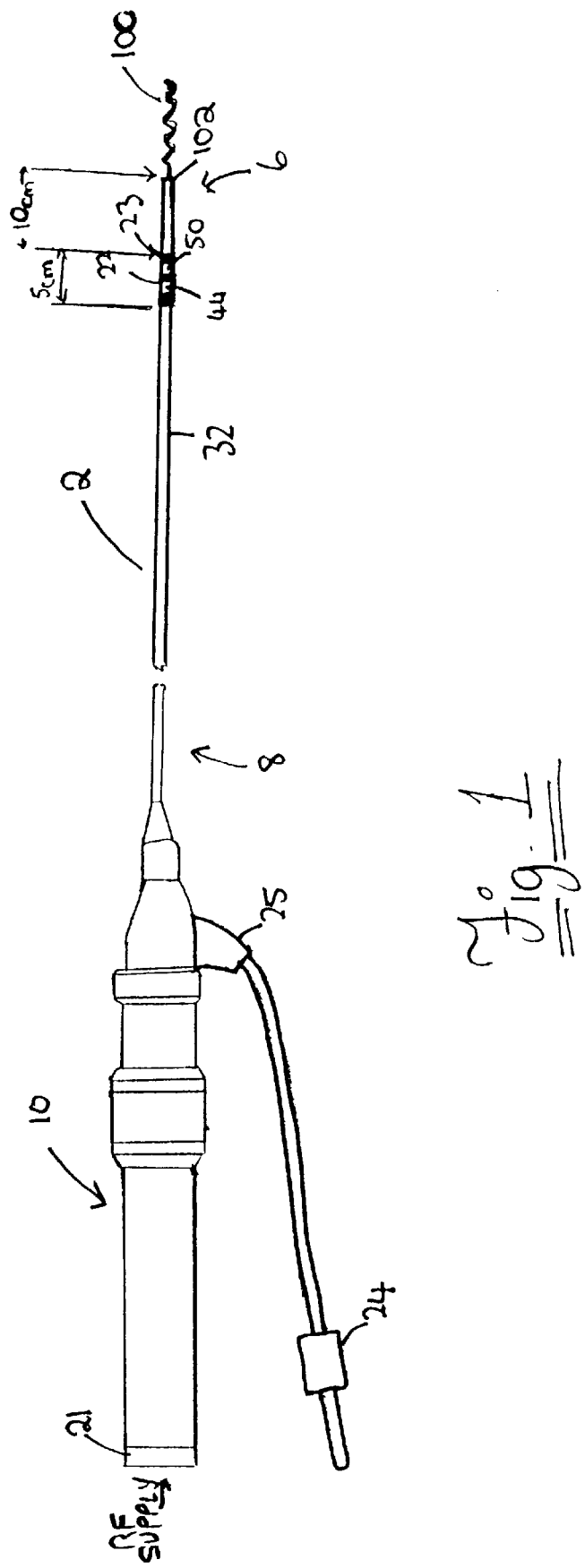
FIG. 1 shows a lead according to the present invention.

The ablation lead or catheter includes a lead body 2 having a distal end 6 and a proximal end 8. The lead or catheter may also have a handle 10 connected to the proximal end. The handle includes an electrical connector 21 connected to electrical conductors. The handle may be of a conventional design or may be a design as described in, for example, U.S. Pat. No. 5,318,525.

Electrodes 22, 23 are provided in an array toward the distal end of the lead. Preferably approximately 10 cm from the screw tip there is provided an array of electrodes over 5 to 6 cm.

High power electrical conductors are connected to the ablation electrodes in a conventional manner, e.g. by soldering or welding. Thermocouple wires may be respectively positioned adjacent to the ablation electrodes to permit the temperatures of the electrodes to be monitored.

The catheter or lead body may comprise three segments, a proximal segment, an intermediate segment and a distal segment. The lead preferably has a shaft body 32 made of Pebax, a polyamide polyether block copolymer made by Elf Atochem, Inc. of Philadelphia, Pa. To impart more flexibility to this section, the Pebax material is a relatively low durometer material e.g. 30–40D. The shaft body 32 includes a central lumen and satellite lumens (not shown) extending along the length of the body 32. A core wire (not shown) fits loosely within the central lumen, while electrical conductors and thermocouple wires pass through other lumen.

The distal end 6 of shaft body 32 lies adjacent an insulator 44 made of PEEK (poly-ether-either-ketone) or other hard, temperature-resistant material. The insulator 44 is bonded to the distal end 6 of the shaft body 32 by heat fusion and adhesive.

A cylindrical ablation electrode 22 is secured to and extends between insulator 44 and second insulator 50. A further electrode 23 is secured to the distal end of the insulator 50.

At the most distal end of the lead is located a helical screw 100, mounted to a plastic tip 102. The helical screw 100 is insulated from electrode 23 and is employed to locate the distal end of the catheter at the desired location.

The helical screw is electrically insulated from the remainder of the catheter.

In use, the catheter may be advanced to its desired location by passing the catheter through a guide catheter of fixed configuration or through a deflectable or deformable guide catheter, in order to locate the distal end of the catheter at a desired location within the heart. Alteratively, a deflectable stylet, or guide may be inserted into the internal lumen and used to control the movement of the catheter through the vascular system.

The helical screw tip 100 is screwed into the right ventricular apex or preferably a little proximal to the apex. The array of electrodes is arranged on the lead body such that when the tip is screwed into place, the RF electrodes overlie the target area between the triscupid annulus and the inferior vena cava.

Fluid fitting 24 is coupled to a source of fluid, such as Ringer's solution which may be diluted by means of a pump to the porous section of electrode 22 and RF energy is applied to electrode 23, by means of electrical connector 25. The delivered Ringer's or other conductive solution serves both to more evenly distribute to the current applied to the electrodes and to cool the tissue adjacent to the electrode, preventing overheating and desiccation of the tissue.

A little further manipulation can then be carried out with the lead tip 100 screwed into position, such that the electrodes 22,23 can also be brought close to the coronary sinus, allowing the other target area between the coronary sinus and the tricuspid annulus to be ablated.

Signals can then be displayed on a multichannel device and ablation delivered where most appropriate with a stable catheter.

A small amount of tension can be applied to the lead so as to keep it close to the right atrial wall during energy delivery.

Figure 2:
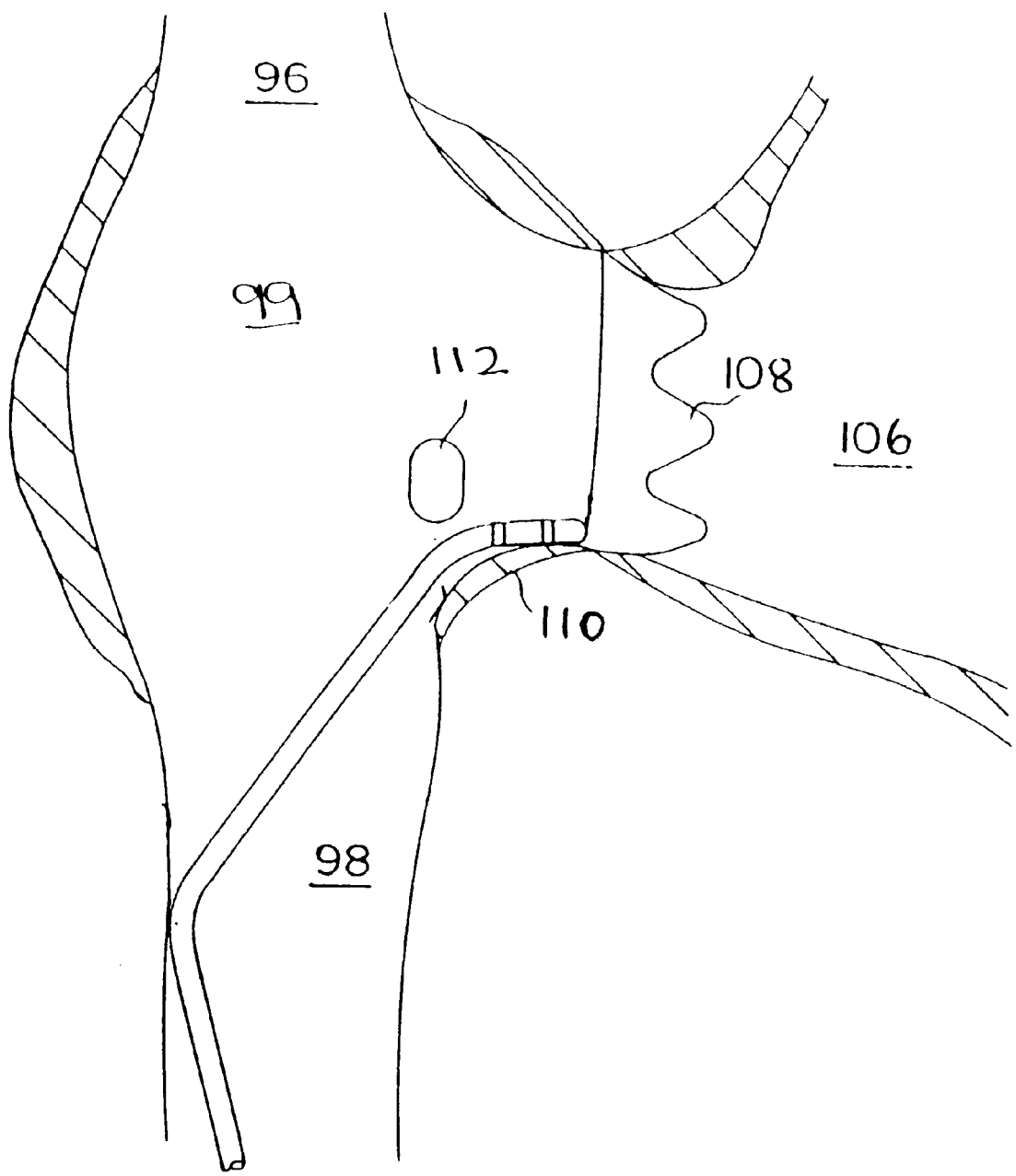
FIG. 2 shows an ablation lead positioned in the heart for treatment of atrial flutter according to the present invention.

FIG. 2 shows, in simplified form, a portion of a heart having a superior vena cava 96 and inferior vena cava 98 opening into a right atrium 99. Also shown is a portion of right ventricle 106 separated from right atrium 99 by a tricuspid valve 108. An isthmus of tissue 110 extends between the inferior aspect of the triscupid valve 108 and inferior vena cava 98 adjacent to the opening of the coronary sinus 112.

The lead is arranged in the heart as described above.

After any appropriate readings are taken, the ablation electrode can be coupled to a suitable RF power supply (not shown). The ablation electrodes are electrically isolated from each other so that they can be independently powered from the power supply. Thus, the power supply need not be as large as would be required if the ablation electrodes were electrically connected to each other, or if one long ablation electrode were used.

After the necessary ablation has been carried out, the lead can be unscrewed from the right ventricle and removed.

The principle of the present invention could also be applied to the performance of the endocardial maze procedure, but different electrode array layouts would be necessary.

The screw-in tip may also be used to fix the lead to the atrial wall instead of in the ventricle.

What is claimed is:

1. An ablation lead for treating atrial flutter, comprising:

a lead body having proximal and distal ends;

a screw tip adapted to be fixed in an apex of a right ventricle of a human heart, the screw tip being disposed at the distal end of the lead body;

an array of electrodes for delivering RF energy, the electrodes and the screw tip being spaced apart from one another, and the electrodes being arranged on the lead body in such a manner, that when the screw tip is affixed In the apex of the right ventricle the electrodes can ablate a first area between the tricuspid annulus and the inferior vena cava of a human heart or a second area between the coronary sinus and the tricuspid annulus, the screw tip being configured to not dislodge from the apex of the right ventricle when the electrodes ablate the first or second areas, the screw tip being electrically isolated from the electrodes.

2. The lead according to claim 1, wherein the screw tip is a 'Bisping type' screw tip.

3. The lead according to claim 1, further comprising a handle attached to the proximal end thereof.

4. The lead according to claim 3, wherein the handle includes an electrical connector connected to electrical conductors.

5. The lead according to claim 1, further comprising thermocouple wires positioned adjacent to the ablation electrodes for enabling the temperatures of the electrodes to be monitored.

6. A lead according to claim 1, further comprising a fluid fitting adapted to be coupled to a source of conductive fluid.

7. A method of treating atrial flutter by ablation of cardiac tissue by employing an ablation lead, the ablation lead comprising proximal and distal ends, a screw tip adapted to be fixed in an apex of a right ventricle of a human heart, the screw tip being disposed at the distal end of the lead body, an array of electrodes for delivering RF energy, the electrodes and the screw tip being spaced apart from one another, and the electrodes being arranged on the lead body in such a manner, that when the screw tip is affixed in the apex of the right ventricle the electrodes can ablate a first area between the tricuspid annulus and the inferior vena cava of a human heart or a second area between the coronary sinus and the tricuspid annulus, the screw tip being configured such that the tip does not become dislodged when the electrodes ablate the first or second areas, the screw tip being electrically isolated from the electrodes, the method comprising:

inserting the ablation lead into the heart and securing the lead tip in the apex of the right ventricle by screwing the lead tip therein such that electrodes overlie the first area or the second area; and applying radiofrequency energy to the first or second areas via the electrodes to cause ablation of the tissue.

\* \* \* \* \*